(12) United States Patent
Paul

(10) Patent No.: US 7,008,426 B2
(45) Date of Patent: Mar. 7, 2006

(54) BONE TREATMENT PLATE ASSEMBLY

(76) Inventor: Kamaljit S. Paul, 3220 Old Orchard La., Oshkosh, WI (US) 54902

( * ) Notice: Subject to any disclaimer, the term of this patent is extended or adjusted under 35 U.S.C. 154(b) by 269 days.

(21) Appl. No.: 10/691,409

(22) Filed: Oct. 22, 2003

(65) Prior Publication Data

US 2004/0097940 A1    May 20, 2004

Related U.S. Application Data

(63) Continuation-in-part of application No. 10/627,065, filed on Jul. 24, 2003, and a continuation-in-part of application No. 10/202,705, filed on Jul. 24, 2002, which is a continuation-in-part of application No. 10/014,409, filed on Dec. 14, 2001, now Pat. No. 6,755,833.

(51) Int. Cl.
*A61B 17/80*        (2006.01)
(52) U.S. Cl. .............................. 606/70; 606/61; 606/69
(58) Field of Classification Search ................... 606/61, 606/69, 70, 71
See application file for complete search history.

(56) References Cited

U.S. PATENT DOCUMENTS

| | | | |
|---|---|---|---|
| 2,406,832 A | 9/1946 | Hardinge |
| 2,486,303 A | 10/1949 | Longfellow |
| 4,246,660 A | 1/1981 | Wevers |
| 4,503,848 A | 3/1985 | Caspar et al. |
| 4,513,744 A | 4/1985 | Klaue |
| 5,324,290 A | 6/1994 | Zdeblick et al. |
| 5,344,421 A | 9/1994 | Crook |
| 5,569,251 A | 10/1996 | Baker et al. |
| 5,578,034 A | 11/1996 | Estes |
| 5,616,142 A | 4/1997 | Yuan et al. |
| 5,616,144 A | 4/1997 | Yapp et al. |
| 5,676,666 A | 10/1997 | Oxland et al. |
| 5,681,311 A | 10/1997 | Foley et al. |
| 5,728,127 A | 3/1998 | Asher et al. |
| 5,876,402 A | 3/1999 | Errico et al. |
| 5,904,683 A | 5/1999 | Pohndorf et al. |
| 5,951,558 A | 9/1999 | Fiz |
| 5,954,722 A | 9/1999 | Bono |
| 6,017,345 A | 1/2000 | Richelsoph |
| 6,030,389 A | 2/2000 | Wagner et al. |
| 6,106,557 A | 8/2000 | Robioneck et al. |
| 6,129,730 A | 10/2000 | Bono et al. |
| 6,139,550 A | 10/2000 | Michelson |

(Continued)

FOREIGN PATENT DOCUMENTS

DE        28 08 971        9/1979

(Continued)

OTHER PUBLICATIONS

"Blackstone™ Anterior Cervical Plate," Blackstone Medical Inc., Product literature, date unknown, 4 sheets.

(Continued)

*Primary Examiner*—David O. Reip
(74) *Attorney, Agent, or Firm*—Wilhelm Law Service, S.C.; Thomas D. Wilhelm

(57) ABSTRACT

Bone treatment plate assemblies, methods of fabrication, and methods of use. Such assemblies comprise spring structures assembled to bone treatment plates. The spring structure comprises elongate bands, and springs between the bands, urging the bands against structure of the plate. Spring width is less than spring height and/or one or more protuberances extending from the band or bands cooperate with one or more detents in the plate thereby to arrest longitudinal movement of the spring structure with respect to the plate.

61 Claims, 5 Drawing Sheets

U.S. PATENT DOCUMENTS

| | | | |
|---|---|---|---|
| 6,152,927 | A | 11/2000 | Farris et al. |
| 6,159,213 | A | 12/2000 | Rogozinski |
| 6,193,721 | B1 | 2/2001 | Michelson |
| 6,224,602 | B1 | 5/2001 | Hayes |
| 6,235,034 | B1 | 5/2001 | Bray |
| 6,238,396 | B1 | 5/2001 | Lombardo |
| 6,241,731 | B1 | 6/2001 | Fiz |
| 6,293,949 | B1 | 9/2001 | Justis et al. |
| 6,306,139 | B1 | 10/2001 | Fuentes |
| 6,364,881 | B1 | 4/2002 | Apgar et al. |
| 6,402,756 | B1 | 6/2002 | Ralph et al. |
| 6,454,771 | B1 | 9/2002 | Michelson |
| 6,458,133 | B1 | 10/2002 | Lin |
| 6,503,250 | B1 | 1/2003 | Paul |
| 6,533,786 | B1 | 3/2003 | Needham et al. |
| 6,602,255 | B1 | 8/2003 | Campbell et al. |
| 6,602,256 | B1 | 8/2003 | Hayes |
| 2002/0151899 | A1 | 10/2002 | Bailey et al. |
| 2003/0018335 | A1 | 1/2003 | Michelson |
| 2003/0045880 | A1 | 3/2003 | Michelson |
| 2003/0083658 | A1 | 5/2003 | Hawkes et al. |

FOREIGN PATENT DOCUMENTS

| | | |
|---|---|---|
| DE | 44 09 833 | 10/1995 |
| EP | 1 169 971 | 1/2002 |
| FR | 1505513 | 12/1967 |
| FR | 2778088 | 11/1999 |
| WO | WO 00/24325 | 5/2000 |
| WO | WO 00/64359 | 11/2000 |
| WO | WO 01/26566 | 4/2001 |
| WO | WO 01/26567 | 4/2001 |

OTHER PUBLICATIONS

"CSLP Variable Angle: For Use with the Cervical Spine Locking Plate System," Technique Guide, 2000 SYNTHES® Spine, 28 sheets.

Zdeblick, M.D., Thomas A. et al. "Premier™ Anterior Cervical Plate System." Surgical Technique, 2000 Medtronic Sofamor Danek, 30 sheets.

Health Journal, Tara Parker-Pope, The Wall Street Journal, Jan. 2001, 1 sheet.

C-TEK Anterior Cervical Plate, 2001 Interpore Cross International, 1 sheet.

C-TEK Anterior Cervical Plate System, Interpore Cross, Oct. 2000, 1 sheet.

WINDOW Cervical Stabilization System, 2000 Endius, Inc., 10 sheets.

Caspar Instruments for Anterior Cervical Fusion, AESCULAP, date unknown, 2 sheets double-sided.

NDC Internet data sheets, date unknown, 3 sheets.

Ni-Ti alloy Internet Data Sheets, printed Dec. 5, 2001, 4 sheets.

AESCULAP, Advanced Biomechanical Concept, date unknown, 11 sheets.

ORIA Zenith, Product Specifications, Mar. 2003, 18 sheets.

ZENITH, the perfect alliance for successful cervical fusions, Internet data sheets downloaded Apr. 2003, 2 sheets.

U.S. Appl. No. 10/014,409, filed Dec. 14, 2001, Bone Support Assembly, 7 sheets double-sided.

"The Market for Spinal Implants," Internet data sheets downloaded May 2001, 4 sheets.

BONE TREATMENT PLATE ASSEMBLY

CROSS-REFERENCE TO RELATED APPLICATIONS

This application claims priority under 35 U.S.C. §120 to application Ser. No. 10/202,705 filed Jul. 24, 2002, and to Ser. No. 10/627,065 filed Jul. 24, 2003 which claims priority to application Ser. No. 10/202,705 filed Jul. 24, 2002 and to application Ser. No. 10/014,409 filed Dec. 14, 2001; all the above of which are incorporated herein by reference in their entireties.

BACKGROUND

The present invention relates to devices for the fixation and/or support of bones. In particular, the present invention relates to a bone treatment plate assembly, a corresponding bone treatment plate, and a spring structure, all directed to treatment of bones of e.g. the spinal column. The plate of the present invention has particular application in situations where compression or settling forces, as well as torsional and flexing forces, of e.g. "fixed" vertebrae on a bone treatment plate, cause significant stressing and potential failure of the bone treatment plate and/or plate components, or unacceptable stressing or other deleterious affect on the bones being treated.

Vertebral fixation has become a common approach to treating spinal disorders, fractures, and the like, and for fusion of vertebrae at the time such fixation is instituted. Namely, one or more vertebrae are fixed in position relative to one or more other vertebrae above and/or below the vertebrae to be fixed. Generally, a bone treatment plate, namely a spinal plate, is the device of choice used for mechanically supporting such vertebral fixation. A typical spinal plate includes a plate having a plurality of apertures therethrough. A plurality of fasteners, i.e., bone screws, are generally positioned into and through respective ones of the apertures of the plate to thereby attach the spinal plate to bone, such as to two or more respective upper and lower supporting adjacent spinal vertebrae. The screws are fastened to the respective support vertebrae to thereby attach the spinal plate to the support vertebrae. In general, such plate and screw assemblies can be utilized, for example, for anterior fixation of the spine for cervical, lumbar, and/or thoracic fixation.

The basis of anterior fixation or plating is to approach the spine from an anterior or anterio-lateral approach, and use the screws to solidly mount the spinal plate to the vertebrae being treated. In addition to the application of a spinal plate, graft material may be combined with the vertebrae, or vertebrae elements, as an assist in permanently fusing together adjacent vertebrae. The graft material can consist of bone graft material obtained from bones of the recipient, or bone graft material obtained from another individual.

A common problem associated with the use of such spinal bone treatment plates is the tendency of the bone screws to "back out" or pull away or otherwise withdraw from the bone into which they are mounted. This problem occurs primarily as a response to the normal torsional and bending motions of the body and spine.

This is a particularly important problem in that, as the screws become loose and pull away or withdraw from the bone, the heads of the screws can rise above the surface of the spinal plate and, possibly, even work their way completely out of the bone. While this condition can cause extreme discomfort for the recipient user of the spinal plate, any substantial withdrawal of the screws from the bone/plate can also create a number of potentially serious physiological problems given the significant amount of nervous and vascular structures located at or near the potential locations of anterior spinal plate fixations.

A number of plate assembly designs have been proposed in attempts to prevent screws from pulling away or withdrawing from the bone and/or to prevent the screws from backing out or pulling away or withdrawing from the surface of the spinal plate. Such mechanisms used to prevent bone screws from pulling out of bones include cams which engage and lock the screws, and the use of expanding head screws which expand outwardly when adequate force is applied thereto to engage the holes in the spinal plate. All of these designs have detriments, which include potential for breakage of the screws, or which require particular precision and alignment in their application in order to work correctly. Additionally, loose components and accessories of spinal plates, which address the "backing-out" or withdrawal problem, can get dropped and/or misplaced while the e.g. vertebral fixation surgical procedure is taking place, prolonging and complicating the procedure which results in increased risk of harm to the recipient.

Yet another common phenomenon associated with the use of such spinal plates is the tendency, of the vertebrae which are being treated, to settle after the spinal plate has been installed. Such settling adds compression forces to the above-listed forces, and raises the probability that one or more of the bone screws will break, will back out, or pull away, or otherwise decouple, from the bone to which such bone screw was mounted.

It is an object of the invention to provide bone treatment plate assemblies which facilitate secure bone-to-bone fixation and/or support, such as at e.g. adjacent or second adjacent vertebrae, while accommodating bone-to-bone settling and axial loading, as well as post-procedural compression between the respective bones.

It is another object of the invention to provide bone treatment plate assemblies which afford substantial protection against pulling away or withdrawal of mounting components, which pulling away or withdrawal may result from e.g. torsional movement, flexing movement, or stress and/or dynamic load sharing of the vertebrae, the protection thereby enhancing the bone rebuilding process carried on routinely by the living body.

It is yet another object of the invention to provide bone treatment plate assemblies which attenuate application of stress on the plate apparatus and on the affixing components.

It is a further object of the invention to provide bone treatment plate assemblies comprising a bone treatment plate and a spring structure having resiliently movable spring-like material having resilient properties, the assemblies being so mounted and positioned as to enable bone fasteners to move past such spring-like material, with corresponding flexing or other movement of such spring-like material, when the bone fasteners are being installed in a recipient user and which, in combination with the designs of the bone fasteners, prevent unintentional withdrawal of the bone fasteners after installation of the bone fasteners in the recipient user.

It is still a further object of the invention to provide a spring structure, in a bone treatment plate assembly comprising a bone treatment plate, wherein the spring structure includes resiliently movable spring-like material having resilient properties, including springs, e.g. straight-line compression springs, wherein the width of a given spring is less than the height of the respective spring.

It is still a further object of the invention to provide a spring, in a bone treatment plate assembly comprising a bone treatment plate wherein the spring structure includes resiliently movable spring-like material having resilient properties, including folded or curvilinear compression springs wherein the width of a given spring is less than the height of the respective spring.

A still further object of the invention is to provide a spring structure for use in a bone treatment plate assembly comprising a bone treatment plate, wherein the spring structure comprises first and second opposing and longitudinally-extending bands, springs between the bands, and locking protuberances extending from the bands and engaging corresponding receiving detents in such plate.

It is yet a further object of the invention to provide bone treatment plate assemblies, such as spinal plate assemblies, which can be completely pre-assembled such that no assembly steps need be performed on the spinal plate assembly, itself, as part of the surgical procedure whereby the spinal plate assembly is being installed in a recipient user thereof.

It is still a further object of the invention to provide bone treatment plate assemblies wherein apparatus, in such bone treatment plate assemblies, for preventing withdrawal of bone fasteners from the bone, after installation of the bone fasteners in a recipient user, are automatically activated, to prevent such withdrawal, as a consequence of the installation of suitably-configured such bone fasteners.

SUMMARY

This invention provides novel spinal plate assemblies, methods of fabricating such e.g. spinal bone treatment plate assemblies, and methods of using such plate assemblies. Such bone treatment plate assembly comprises a spring structure assembled to a bone treatment plate. The spring structure comprises first and second elongate bands, biased against each other, by springs which extend between the plates, and resiliently urges the bands away from each other when the bands are urged toward each other by an outside force. The bands are juxtaposed proximate, and extend into, fastener-receiving-apertures in the bone treatment plate. Widths of the springs are collectively less than heights of the springs, whereby the ratio of spring width to spring height is less than 1/1; and/or protuberances extend from one or both bands, and engage detents in the plate, thereby to arrest and/or prevent longitudinal movement of the spring structure relative to the plate.

In a first family of embodiments, the invention comprehends a spring structure having first and second ends, a length, a structure top and a structure bottom, and a structure height therebetween. The spring structure further comprises first and second bands each having first and second ends, a band top, and a band bottom associated with the structure top and the structure bottom, the bands having respective lengths, the first and second bands each having an outer surface facing outwardly of the spring structure, and an inner surface, the inner surfaces facing each other and facing inwardly into the structure, the first and second bands defining a width of the spring structure between the outer surfaces; and springs spaced along the length of the spring structure, the springs extending between and connected to the bands, and having spring lengths extending between the first and second bands, the springs having spring tops and spring bottoms, opposing spring sides, spring heights between the spring tops and the spring bottoms, spring widths between the opposing spring sides, angles $\alpha$ being defined between the springs and the inner surfaces of the bands, and angles $\beta$ being defined between the band tops and the spring tops, ratio of the widths of the springs to the heights of the springs being less than 1/1 whereby, when a squeezing force is imposed on the spring structure, squeezing the first and second bands toward each other, the springs deflect so as to accommodate reduced width of the spring structure in preference to deflecting in a direction corresponding to the height, such that the response of the spring structure to such squeezing force is a preferential change in magnitude of angle $\alpha$ relative to change in magnitude of angle $\beta$.

In preferred embodiments, when the squeezing force is imposed on the spring structure, change in magnitude of angle $\beta$ is substantially zero. In preferred embodiments, the ratio of spring width to spring height is no more than 0.8/1, more preferably about 0.15/1 to about 0.7/1, still more preferably about 0.2/1 to about 0.5/1, and most preferably about 0.25/1 to about 0.35/1. The lower ones of the ratios typically provide the relatively greater divergence between the changes in magnitudes of angles $\alpha$ and $\beta$.

In some embodiments, the springs are arranged in groups of at least two springs, preferably at least three springs along the bands.

In some embodiments, the springs comprising (i) at least three groups of springs wherein each group comprises at least two springs, and wherein spacing between the springs in a group is less than spacing between the groups, or (ii) at least 6 individual springs substantially equally spaced from each other.

In some embodiments, the springs comprise folded springs.

In other embodiments, the springs comprise substantially straight line compression springs.

In some embodiments, the compositions of the first and second bands and/or the compositions of the springs comprise at least one of titanium, titanium alloy, and stainless steel.

In preferred embodiments, the first and second bands, in combination with the springs, define a unitary structure derived from a single unitary work piece.

In some embodiments, the spring structure, or elements of the spring structure such as the bands and/or the springs, comprise plastic composition which is safe for use in living human or animal bodies, as an implantable plastic, and wherein the spring structure has suitable strength, rigidity, and deflection properties to block screw withdrawal in a routine implant use environment.

In preferred such embodiments, the plastic composition of the spring structure comprises one or more materials selected from the group consisting of polyetherimide copolymer, acetal copolymer, polyethersulfone, polyarylethersulfone, polycarbonate, ultra high molecular weight polyethylene, polyetheretherketone, and polyaryletherketone, and blends and mixtures of the materials.

In preferred embodiments, at least one of the bands comprises a movement-arresting protuberance extending outwardly therefrom.

In some embodiments, the bands comprise first and second protuberances extending from the bands and being effective, in combination with cooperating detents in a cooperating structure, and wherein the spring structure is otherwise confined with respect to such other cooperating structure, to arrest longitudinal movement of the spring structure along such other cooperating structure.

In some embodiments, the bands comprise first and second protuberances extending from the bands at or proximate the first ends of the bands, and third and fourth protuberances extending from the bands at or proximate the second ends of the bands, the first, second, third, and fourth protuberances collectively being effective, in combination with a cooperating detent in another cooperating structure, and wherein the spring structure is otherwise confined with respect to such other cooperating structure, to arrest longitudinal movement of the spring structure along such other cooperating structure.

In a second family of embodiments, the invention comprehends a bone treatment plate assembly, comprising a bone treatment plate, the bone treatment plate comprising a top and a bottom, and a plurality of bone-fastener-receiving apertures, the bone treatment plate further comprising a thickness between the top and the bottom, a channel extending alongside respective ones of the apertures, the channel having a collective length, and a side wall, the side wall of the channel having an opening therein extending into a respective one of the fastener-receiving apertures; and spring structure in the channel, the spring structure having first and second ends, a length, a structure top and a structure bottom, and a structure height therebetween, the spring structure further comprising (i) first and second bands each having first and second ends, a band top, and a band bottom associated with the structure top and the structure bottom, the bands having respective lengths thereof, the first and second bands each having an outer surface facing outwardly of the spring structure, and an inner surface, the inner surfaces facing each other and facing inwardly into the spring structure, the first and second bands defining a width of the spring structure between the outer surfaces, and extending along the length of the channel in the bone treatment plate, and (ii) springs spaced along the length of the spring structure, the springs extending between and connected to the bands, and having spring lengths extending between the first and second bands, the springs having spring tops and spring bottoms, opposing spring sides, spring heights between the spring tops and the spring bottoms, spring widths between the opposing spring sides, angles α being defined between the springs and the inner surfaces of the bands, and angles β being defined between the band tops and the spring tops, the springs urging the spring structure into engagement with the side wall of the channel, ratio of the widths of the springs to the heights of the springs being less than 1/1, whereby, when a squeezing force is imposed on the spring structure, squeezing the first and second bands toward each other, sufficient to assemble the spring structure to the bone treatment plate, the springs deflect so as to accommodate reduced width of the spring structure in preference to deflecting in a direction corresponding to height, such that the response of the spring structure to the squeezing force is a preferential change in magnitude of angle α relative to change in magnitude of angle β.

In some embodiments, when the squeezing force is imposed on the spring structure, change in magnitude of angle β is substantially zero.

In some embodiments, the first and second bands extend along substantially the entirety of the length of the channel, the first and second bands collectively extend into and across portions of each of the bone-fastener-receiving apertures.

In some embodiments, the side wall of the channel comprises a first side wall, the channel further comprising a second side wall, the bone treatment plate further comprising first and second rows of the bone-fastener-receiving apertures extending along the length of the bone treatment plate, the channel extending along the length of the bone treatment plate, the channel further comprising a second side, first and second overhanging top walls of the channel extending inwardly from the side walls of the channel, the overhanging top walls being effective to restrain movement of the spring structure out of the channel through the top of the channel, the first and second elongate bands preferably being urged by the spring structure against the respective first and second side walls of the channel, and thus across a portion of each respective aperture in the first and second rows.

In preferred embodiments, as a bone fastener is driven, the bone fastener urges the respective band to move, from a first position transversely of the length of the band, with corresponding flexing of the spring structure, from a first flexural condition, until the bone fastener moves past the band, whereupon the spring structure returns the band to a position wherein the band overlies and blocks the bone fastener and thereby inhibits withdrawal of the bone fastener past the band.

In preferred embodiments, the bands are sufficiently small in cross-section, and are properly positioned over the apertures, and the spring structure is sufficiently resilient, to let a bone fastener pass below a respective one of the bands, with transverse movement of the band, and without exceeding any flexural limit of the spring structure, such that the spring structure then resiliently returns the band to a blocking position over the bone fastener.

In some embodiments, the channel is expressed intermittently along the length of the plate.

In some embodiments, the bone-fastener-receiving apertures are spaced along the length of the bone treatment plate, the channel is elongate and extends along the length of the bone treatment plate, the spring structure comprises a plurality of band-spring combinations, each comprising ones of the bands and ones of the springs, positioned in the channel, the band-spring combinations being disposed lengthwise of each other, and disposed alongside respective ones of the apertures, spacers being positioned between respective adjacent ones of the band-spring combinations so as to inhibit substantial longitudinal movement of the band-spring combinations.

In some embodiments, the spacers are held in position in the channel by protuberances on ones of the bands and/or the spacers, which protuberances cooperate with detents in the channel.

In preferred embodiments, the channel comprises a plurality of walls, including the side wall, extending at least intermittently along the length of the channel, at least one of the bands comprising at least one protuberance, the walls of the channel collectively comprising at least one cooperating detent, optionally at least first and second detents, configured and positioned to receive the at least one protuberance on the respective at least one band, the at least one protuberance and the at least one detent thereby being effective to arrest longitudinal movement of the spring structure along the length of the channel as the spring structure is moved along the bone treatment plate.

In preferred such embodiments, the detent arrests longitudinal movement of the spring structure when the entirety of the length of the spring structure has been received into the channel.

In some embodiments, the channel comprises a plurality of walls, including the side wall, extending along the length of the channel, first and second protuberances extending from the bands on opposing sides of the spring structure and toward respective ones of the walls of the channel, the walls of the channel comprising at least first and second detents, configured and positioned to receive the protuberances, the combination of the first and second protuberances and the first and second detents being effective to arrest longitudinal movement of the spring structure along the length of the channel.

In preferred embodiments, the first and second protuberances extend outwardly from the outer surfaces of the bands.

In some embodiments, the first and second protuberances are disposed at the first end of the spring structure.

In some embodiments, the bone treatment plate assembly further comprises third and fourth protuberances at the second end of the spring structure, and cooperating third and fourth detents in the walls of the channel.

In some embodiments, at least one protuberance and at least one cooperating detent are collectively configured to arrest longitudinal movement of the respective spring structure or band-spring combination in either of two opposing longitudinal directions.

In some embodiments, the at least one protuberance comprises a single protuberance and/or the at least one detent comprises a single detent, whereby the single protuberance or single detent is configured to arrest or otherwise restrict longitudinal movement of the spring structure in either of the two longitudinal directions possible in the channel.

In a third family of embodiments, the invention comprehends a spring structure having first and second ends, a length, a structure top and a structure bottom, and a structure height therebetween. The spring structure comprises first and second bands each having first and second ends, a band top, and a band bottom associated with the structure top and the structure bottom, the bands having respective lengths, the first and second bands each having an outer surface facing outwardly of the spring structure, and an inner surface, the inner surfaces facing each other and facing inwardly into the structure, the first and second bands defining a width of the spring structure between the outer surfaces; and springs spaced along the length of the spring structure, the springs extending between and being connected to the bands, and having spring lengths extending between the first and second bands, the springs having spring tops and spring bottoms, opposing spring sides, spring heights between the spring tops and the spring bottoms, and spring widths between the opposing spring sides, the spring structure comprising at least one protuberance extending outwardly from the outer surface of a respective one of the bands, the at least one protuberance being effective, in combination with cooperating at least one detent in a cooperating structure, and wherein the spring structure is otherwise confined with respect to such other cooperating structure, to arrest longitudinal movement of the spring structure along the other cooperating structure.

In some embodiments, the bands comprise first and second protuberances extending from the bands at or proximate the first ends of the bands, and third and fourth protuberances extending from the bands at or proximate the second ends of the bands, the first, second, third, and fourth protuberances collectively being effective, in combination with cooperating detents in another cooperating structure, and wherein the spring structure is otherwise confined with respect to such other cooperating structure, to arrest longitudinal movement of the spring structure along the other cooperating structure.

In some embodiments, angles $\alpha$ are defined between the springs and the inner surfaces of the bands, and angles $\beta$ are defined between the band tops and the spring tops, and ratio of the widths of the springs to the heights of the springs is less than 1/1, whereby response of the spring structure to a squeezing force, squeezing the bands toward each other, is a preferential change in magnitude of angle $\alpha$ relative to change in magnitude of angle $\beta$.

In a fourth family of embodiments, the invention comprehends a bone treatment plate assembly, comprising a bone treatment plate, the bone treatment plate comprising a top and a bottom, and a plurality of bone-fastener-receiving apertures, the bone treatment plate further comprising a thickness between the top and the bottom, a channel extending alongside respective ones of the apertures, the channel having a collective length, and having walls extending at least intermittently along the length of the channel; and spring structure in the channel, the spring structure having first and second ends, a length, a structure top and a structure bottom, and a structure height therebetween, the spring structure further comprising (i) first and second bands each having first and second ends, a band top, and a band bottom associated with the structure top and the structure bottom, the bands having respective lengths thereof, the first and second bands each having an outer surface facing outwardly of the spring structure, and an inner surface, the inner surfaces facing each other and facing inwardly into the spring structure, the first and second bands defining a width of the spring structure between the outer surfaces, and extending along the length of the channel in the bone treatment plate, and (ii) springs spaced along the length of the spring structure, the springs extending between, and being connected to the bands, and having spring lengths extending between the first and second bands, the springs having spring tops and spring bottoms, opposing spring sides, spring heights between the spring tops and the spring bottoms, and spring widths between the opposing spring sides, at least one of the bands comprising a protuberance, the walls of the channel collectively comprising at least one detent configured and positioned to receive the protuberance on the respective band, the combination of the at least one protuberance and the at least one detent being effective to arrest longitudinal movement of the spring structure along the length of the channel as the spring structure is advanced along the channel.

In some embodiments, the bands comprise first and second protuberances extending from the bands at or proximate the first ends of the bands, and third and fourth protuberances extending from the bands at or proximate the second ends of the bands, the first, second, third, and fourth protuberances collectively being effective, in combination with the walls of the plate, and wherein the spring structure is otherwise confined with respect to the channel, to arrest longitudinal movement of the spring structure with respect to the channel.

Figure 1:
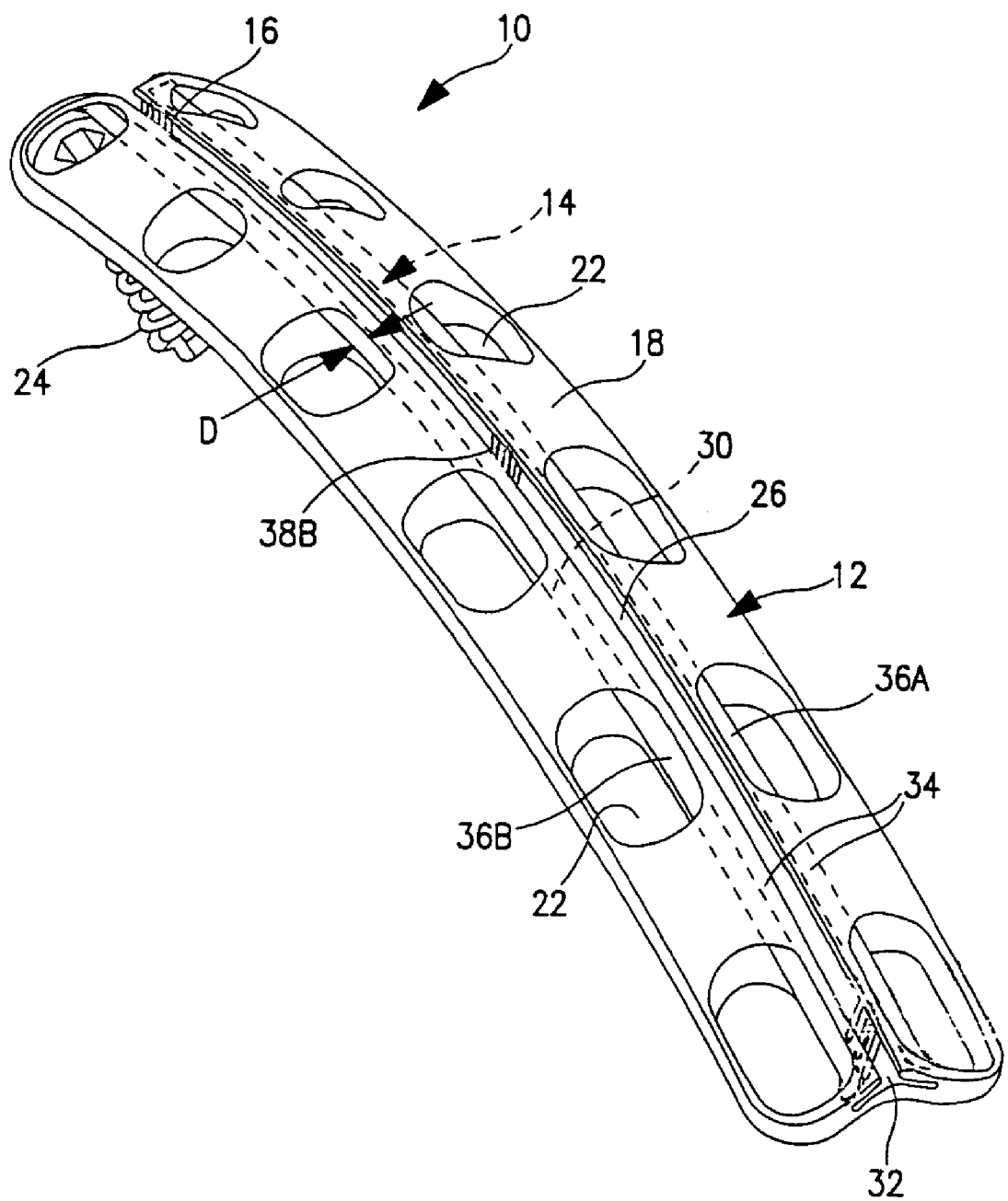
FIG. 1 shows a pictorial view of a first embodiment of bone treatment plate assemblies of the invention, including a bone treatment plate.

The invention is not limited in its application to the details of construction or the arrangement of the components set forth in the following description or illustrated in the drawings. The invention is capable of other embodiments or of being practiced or carried out in other various ways. Also, it is to be understood that the terminology and phraseology employed herein is for purpose of description and illustration and should not be regarded as limiting. Like reference numerals are used to indicate like components.

DESCRIPTION OF THE ILLUSTRATED EMBODIMENTS

Referring now to the embodiments represented by FIGS. 1–6 and 7A, a bone treatment plate assembly 10 of the invention includes a spinal plate 12, which functions as a bone treatment plate, supporting cooperating bone structure in a recipient user. Assembly 10 further includes a spring structure generally represented by 14 in FIGS. 1 and 7A.

Spinal plate 12 has a top surface 18, a bottom surface 20 adapted to be positioned adjacent bone structure of a recipient user of the spinal plate assembly, and a plurality of bone-fastener-receiving apertures 22 which receive bone fasteners such as bone screws 24. Apertures 22 are arranged in first and second rows of such apertures, along the length of the spinal plate.

Figure 9A:
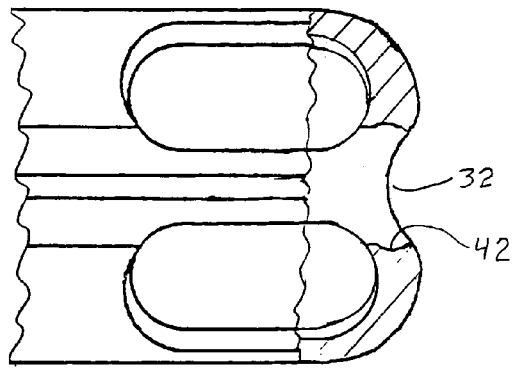
FIG. 9A shows a top view of an enlarged portion of an end section of the bone treatment plate of FIG. 2, with parts cut away.
Figure 9B:
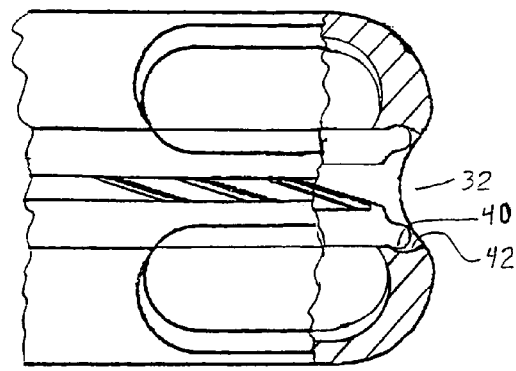
FIG. 9B shows a top view as in FIG. 9A, with the spring structure of FIG. 7A assembled into the plate channel.

Top surface 18 of the spinal plate defines a channel 26 extending along the length of the spinal plate. Channel 26 has a bottom wall 28, opposing side walls 30, and has openings 32 extending out the respective ends of spinal plate 12, best illustrated in FIGS. 1, 9A, and 9B. Channel 26 further has overhanging top walls 34 extending inwardly from the side walls of the channel and spaced from each other and from the bottom wall, thereby leaving an opening 35 in the top of the channel between the overhanging top walls, and extending along the length of the channel. Opening 35 can be eliminated if desired so long as adequate structure is employed to hold spring structure 14 in proper position in channel 26. The cross-sectional area 37 of the open cross-section of the channel, as defined between side walls 30 and top and bottom walls 28 and 34, is preferably generally constant along substantially the full length of plate 12. Side walls 30 of the channel are specifically located and configured so as to open into the sides of, and extend along and inwardly of the sides of, apertures 22. In general, imaginary extensions of side walls 30 project across apertures 22 at locations displaced inwardly of the aperture side walls by distances "D" of about 1 mm.

Figure 7A:
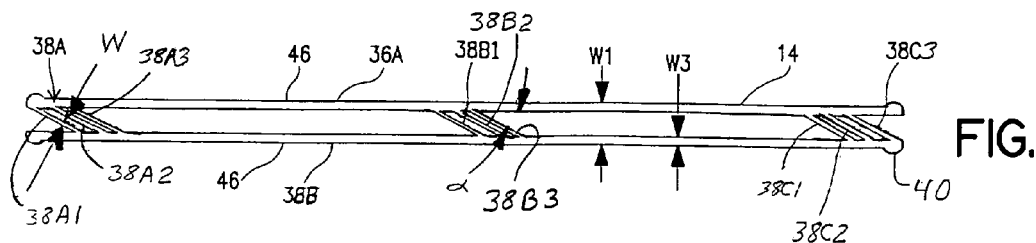
FIG. 7A shows a top view of a first embodiment of spring structures which are incorporated into bone treatment plate assemblies of the invention, and wherein the springs are shown in groups of three.

FIG. 7A illustrates a preferred embodiment of spring structure 14 which is incorporated into the assembly illustrated in FIG. 1. As seen in FIG. 7A, spring structure 14 includes first and second elongate bands 36A, 36B extending parallel to each other and in a common plane or in a common curvilinear surface. Bands 36A, 36B are connected to each other by three groups 38A, 38B, 38C. Thus, group 38A includes springs 38A1, 38A2, 38A3. Group 38B includes springs 38B1, 38B2, and 38B3. Group 38C includes springs 38C1, 38C2, and 38C3. In the embodiment illustrated in FIG. 7A, springs 38 are substantially straight line compression springs connected to bands 36A, 36B at generally straight line acute angles α, as seen in the top view, of about 10 degrees to about 30 degrees, e.g. about 15 degrees to about 20 degrees, to the respective bands. Referring to FIG. 10A, the top of each spring 38A, 38B, 38C also forms an angle β with the tops of respective bands 36A, 36B.

Groups 38A, 38B, 38C of springs represent only one of a wide variety of options for extending compression springs between the bands for biasing the bands against each other and thus for urging the bands away from each other. While 3 groups of springs are shown, any number of springs can be used in a wide array of possible groupings, with suitable adjustment of the force exerted by each spring. Correspondingly, a greater, or lesser, number of groups of springs can be employed.

As used herein, a group of springs is a collection of adjacent springs, namely two or more springs, which are substantially more closely spaced with respect to each other than to other next adjacent springs.

The spring structure, including bands 36 and the individual springs generally designated with the digits 38, is preferably fabricated from a single unitary generally planar work piece, of generally uniform thickness "H". In such instance, the thickness or height "H" of spring structure 14 also is the height "H" of the respective springs 38. The heights of the springs can be greater than, or less than, the heights of the bands, but such is not normally the case.

Spring structure 14 is preferably fabricated from a single sheet of material. Preferred method of fabricating the spring structure is to use laser cutting apparatus to cut away waste material so as to leave bands 36 and springs 38 as suggested at e.g. FIGS. 7A, 7B, and 7C.

Figure 10:
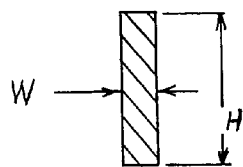
FIG. 10 is a cross-section of a leaf element of a spring of FIG. 7A, illustrating the ratio of width to height of the spring.
Figure 10A:
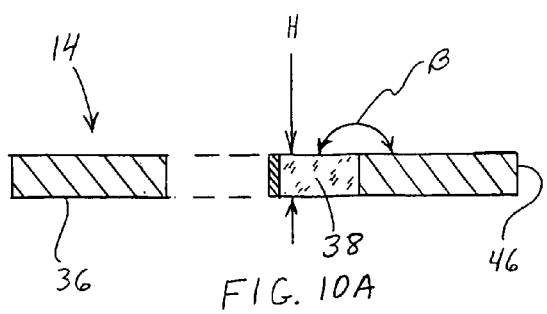
FIG. 10A is a cross-section of the spring structure of FIG. 7B, taken at 10A—10A of FIG. 7B.

In preferred expressions of this invention, the width "W" of spring elements 38, as illustrated in FIGS. 7A and 10, are less, preferably substantially less, than the heights "H" of the respective spring elements. Stated another way, the average width "W" is less than the average height "H". In preferred embodiments, the width "W" of each spring element is less than the height "H" of the respective spring element. Thus, the ratios of width "W" to height "H" are preferably less than 1/1. In typical embodiments, and as illustrated in FIG. 10, the W/H ratio, for a given spring is about 0.15/1 to about 0.7/1, whereas more preferred embodiments employ W/H ratios of about 0.2/1 to about 0.5/1. Most preferred embodiments employ W/H ratios of about 0.25/1 to about 0.35/1. Accordingly, the bending resistance of a given spring in the width direction "W", e.g. in the rest plane of the spring structure, e.g. as the bands are squeezed toward each other, is less than the bending resistance of that spring in the height direction "H", namely a direction which would take the springs out of the plane or planes of band or bands 36.

Figure 4:
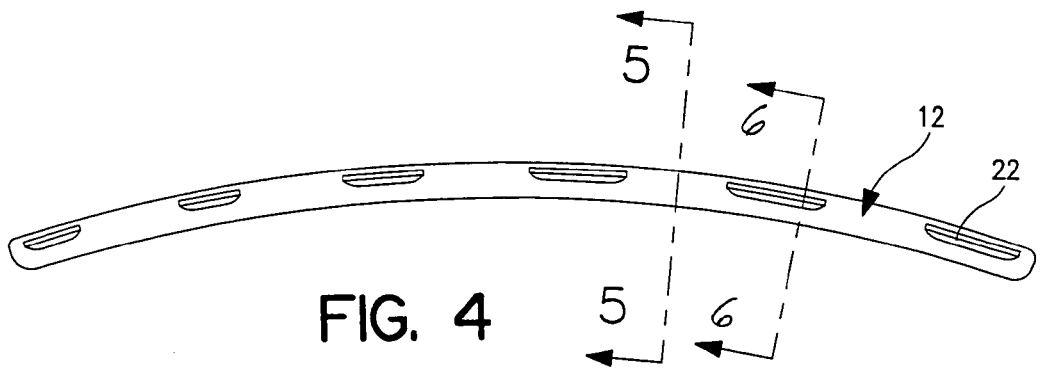
FIG. 4 shows a side view of the bone treatment plate assembly illustrated in FIG. 1.
Figure 5:
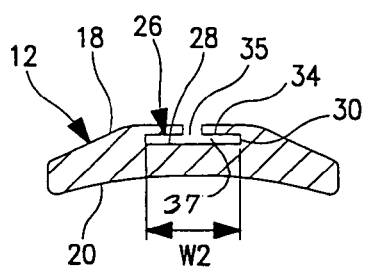
FIG. 5 shows a cross-section of the bone treatment plate illustrated in FIGS. 1–4, and is taken at 5—5 of FIG. 4.

As used herein, "plane" as applied to the spring structure, especially to bands 36, includes moderately curved surfaces such as those illustrated in FIGS. 1 and 4. However, the materials of both bands 36 and springs 38 are resilient whereby a truly flat planar structure can readily conform to the modest curvature of a plate 12 configured with the modest curvature of the plates of FIGS. 1 and 4.

Given the moderate rest magnitude of angle α, at least a substantial vector of the width "W" of the spring element is aligned with the width "W1" of the spring structure. Accordingly, given the relative bending resistances in the "W" and "H" directions, when a force is exerted against the spring structure, generally along the direction of width "W1", thus to urge bands 36A, 36B toward each other, the spring structure tends to respond by collapsing inwardly thereby to reduce width "W1" of the spring structure, thereby reducing the magnitude of angle α in preference to changing the magnitude of angle β. While suitably sensitive instrumentation can likely measure some deflection in angle β, such change in angle β preferably approximates zero. Meantime, change in angle α is desired to be substantial. Thus, the ratio of change in angle α to change in angle β, when a squeezing force, which is not a collapsing force, is exerted on bands 36A, 36B, is preferably substantially greater than 1/1 and can approach infinity. As the ratio of width "W" of the spring to height of the spring is increased, the ratio of such change in angle α to change in angle β decreases. Such α/β ratio is preferably at least 3/1, more preferably at least 10/1. Correspondingly, any width/height ratio of the spring of less than 1/1 is an improvement over known art, and thus within the scope of the invention. Thus, a width to height ratio of e.g. 0.8/1 is within the scope of the invention. Indeed, any spring 38 which exhibits a width to height ratio of less than 1/1, and which shows a preference for change of angle α in preference to angle β is within the scope of the invention By contrast, since resistance to bending in the "H" direction is relatively greater than resistance to bending in the "W" direction, namely bending the spring in the relatively larger "H" dimension of the spring is more difficult than bending the spring in the relatively smaller "W" dimension of the spring, the bands remain in a generally common plane while the bands move into a converging/diverging relationship with respect to each other when a compressive/squeezing force is applied to the outer edges of the spring structure.

In the illustrated embodiments, all the springs have the same widths "W". In other embodiments, not shown, widths of the springs varies from spring to spring; while the average W/H ratio is substantially less than 1/1.

Figure 7B:
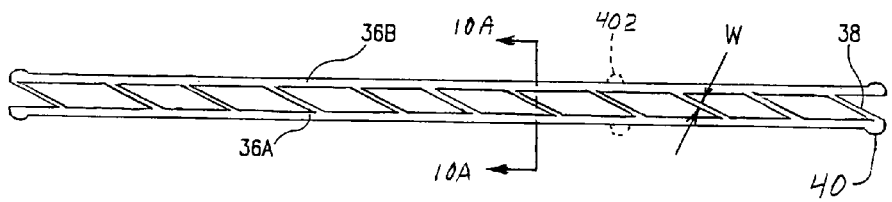
FIG. 7B shows a top view of a second embodiment of spring structures which are incorporated into bone treatment plate assemblies of the invention, and wherein the springs are generally evenly spaced along the length of the spring structure.
Figure 7C:
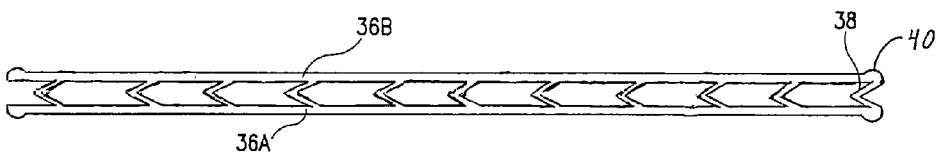
FIG. 7C shows a top view of a third embodiment of spring structures which are incorporated into bone treatment plate assemblies of the invention, wherein the springs are folded leaf constructs which are generally evenly spaced along the length of the spring structure.

FIG. 7A illustrates three springs in each group of springs. A lesser or greater number of springs can be used as desired in each group. Indeed, the number of springs in a respective spring structure can also be selected as desired, and can be more or less than the numbers of springs illustrated in the drawings. For example, FIG. 7A shows 9 springs whereas FIGS. 7B and 7C show 11 springs.

Where groupings are used as illustrated in FIG. 7A, it is preferred that the collective total of the widths "W" of a given group of springs is not substantially greater than the height "H" of the spring structure. The total of the widths of the springs determines the overall resistance to compression/squeezing force. However, where a group is loosely defined in terms of the springs being spread out over a relatively larger length of the spring structure, for example all springs evenly spaced from each other as shown in FIGS. 7B and 7C, adjustment must be made to the foregoing statement to account for the spacing of the springs.

Where the collective total width "W" of a grouped set of springs is on the upper side of the W/H range, resistance to squeezing the spring structure, as affected by a given such spring, e.g. for assembly into the plate, is relatively greater. Accordingly, in such case, and depending on the material from which the springs are fabricated, in some instances, a smaller number of springs can be used for each spring group.

In the alternative, whereas FIG. 7A shows three groups of springs, a greater number of groups can be employed by using a smaller number of springs in each of the respective groups or by reducing e.g. the average spring width "W". The number of springs can be the same for all groups, or can vary as desired, from group to group. As an ultimate expression of the number of groups, each group can include only a single spring as illustrated in FIGS. 7B and 7C, wherein the springs are more or less uniformly spaced from each other.

The width "W" of spring structure 14 between the outer walls 46 of bands 36A, 36B is greater at rest than the width "W2" of channel 26 between side walls 30. Spring structure 14 is inserted longitudinally into channel 26 by squeezing the spring structure together at the width dimension thereof, preferably at an end of the spring structure, sufficient to temporarily reduce the width "W1" of the spring structure at the respective end to a width less than width "W2" of channel 26; and by inserting the reduced-width squeezed end of the spring structure into the end opening 32 at the end of channel 26. As the spring structure is squeezed, the squeezing is progressively resisted by the resilience of the compression springs, e.g. springs 38A or 38C, using the FIG. 7A structure, between the bands. The spring or springs closest to the end being squeezed together is typically most affected, and is therefore most effective in resisting such squeezing, thereby setting up a resilient force urging restitution of the compressive squeezing force, and thus urging the outer walls 46 of the spring structure into engagement with side walls 30 of the channel as the spring structure is inserted longitudinally into channel 26. As the insertion of the spring structure progresses into channel 26, the respective compression springs 38 become progressively squeezed as the springs enter channel 26, each preferably developing a resilient outwardly-directed force urging the outer walls 46 of the bands into engagement with side walls 30 of the channel.

Since the side walls of the channel open into apertures 22, bands 36A, 36B extend across the respective apertures 22 as the spring structure is inserted into channel 26. The length of spring structure 14 as illustrated corresponds substantially with the length of channel 26 such that the entirety of the length of the spring structure is received within channel 26 in the illustrated embodiments, and wherein the spring structure extends substantially the full length of channel 26. Where a single spring structure is used, the length of the spring structure should be at least great enough that bands 36A, 36B extend across each of the apertures 22 in each row of apertures.

Figure 12:
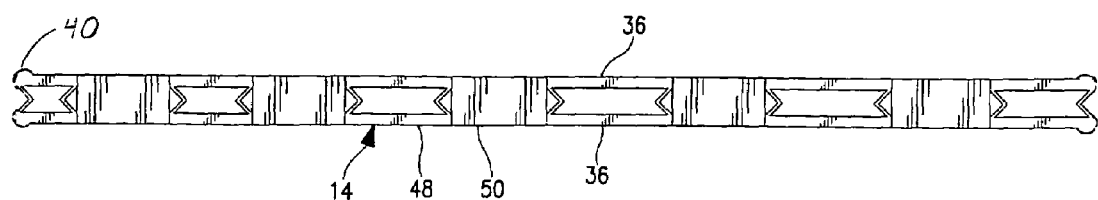
FIG. 12 shows a top view of a segmented spring structure combination employing spacers between a multiplicity of relatively shorter-length spring structures.
Figure 13:
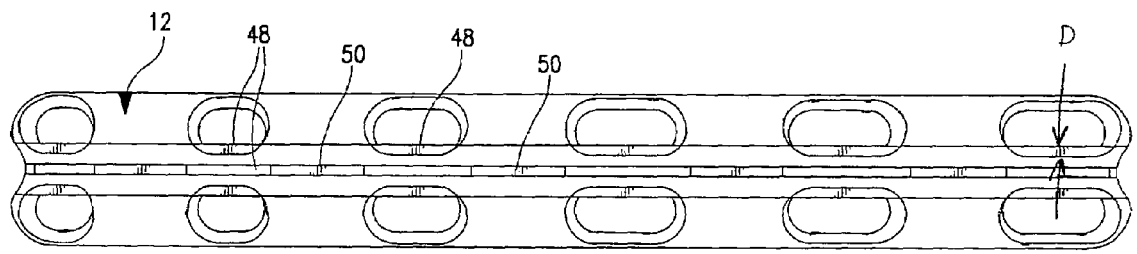
FIG. 13 is a top view of a bone treatment plate assembly of the invention employing the segmented spring structure combination of FIG. 12.

In the alternative, channel 26 can be expressed intermittently. As illustrated in FIGS. 12 and 13, intermittent expression of the channel can be effected by placing spacers 50 in the channel at spaced locations, between respective foreshortened expressions of the spring structure. In an embodiment not shown, channel 26, itself, is intermittent, whereby the space shown occupied by spacers 50 in FIGS. 12, 13 is occupied, in the plate assembly, by material forming part of the structure of plate 12. Thus, channel 26 in such embodiments is expressed as a series of longitudinally spaced, and relatively shorter channels. Length of a given channel is sufficient to hold a spring or spring structure which extends into a respective adjacent aperture 22.

The intensity of resistance of spring structure 14 to compressive force, and intensity of resilient urging of bands 36 against the sides of channel 26, are influenced by the number and distribution of the springs along the length of the spring structure as well as by the selection of the material from which the spring structure is fabricated. The intensity of the spring effect, e.g. the collective spring constant of the corresponding spring structure, when a squeezing force is applied to bands 36A, 36B, is also affected by the collective widths "W" of the respective springs.

Each spring 38, in general, can have a constant height "H" and a constant width "W" along the length of the given spring; or an effective height "H" and an effective width "W". In some embodiments, width "W" of a spring 38 has a modest taper of e.g. about 5 degrees such that spring width "W" is less adjacent the respective bands than toward the mid-point of the length of the spring, whereby bending of the spring is relatively more concentrated adjacent bands 36. Typically, the springs are evenly spaced along the length of the spring structure, or spring groups are evenly spaced along the length of the spring structure.

Typically, all, or nearly all, of the springs in a given spring structure have a common cross-section and a common end-to-end line of progression. A common line of progression is a straight line, as illustrated in FIGS. 7A, 7B. Another line of progression is a folded back, or folded spring, or "V"-shaped spring, all being alternative nomenclatures for the structure illustrated in FIG. 7C. Still another, but not limiting, type of line of progression, not shown, is a curvilinear structure. In any event, the W/H ratio is preferably within the above-noted ranges, thereby to facilitate maintaining bands 36A, 36B in a common plane as spring structure 14 is compressed and assembled into plate 12 at channel 26. Width and/or height can, of course, be varied along the line of progression whereupon the functionally equivalent constant width and/or constant height, in terms of deflection, is used to calculate the W/H ratio.

Referring to especially FIGS. 7A–7C and 9A–9B, protuberances 40 extend outwardly from outer walls 46 on opposing sides of the spring structure 14. In the embodiments illustrated, two protuberances are located at each end of the spring structure. Side walls 30 have detents 42 which cooperate with protuberances 40 to arrest/stop longitudinal movement of side structure 14 along channel 26.

In assembling the spring structure to the plate, an end of the spring structure is squeezed together e.g. to reduce width "W1" such that the width of the spring structure across the protuberances on the respective end 32 of the channel is no greater than the width of the channel at that end of the plate. With the width "W1" so reduced, the spring structure is then inserted longitudinally into channel 26 and pushed along the length of the channel. As the spring structure is pushed longitudinally into the channel, the progression of groups 38 along the length of the spring structure are progressively squeezed by the channel side walls as the respective springs enter channel 26; and the springs correspondingly urge the outer walls 46 of the bands 36 toward outer side walls 30 of the channel, and the protuberances at the leading end slide along and against side walls 30 of the channel. Thus, springs 38 push the leading protuberances into sliding engagement with side walls 30 at least by the time the full length of the spring structure is received into channel 26.

By the time all of the springs are within channel 26, all of the corresponding compression springs are to some degree compressed whereby bands 36A, 36B are urged against side walls 30 along all, or substantially all, of the length of the channel. As the leading end of the spring structure reaches the distal end of the plate, and with springs 38 at the leading end of the spring structure exerting outwardly directed forces, urging bands 36A, 36B away from each other, protuberances 40 at the distal end of the channel are effectively pushed into the detents 42 which are located at the distal end of the channel.

At about the same time, the protuberances at the proximal end of the channel come into engagement with the detents 42 at the proximal end of the channel. The engagement between the protuberances and the detents at the proximal end of the channel arrest the ongoing longitudinal movement of the spring structure so as to stop forward, engaging movement of the spring structure. Meantime, the protuberances and detents at the leading end of the spring structure and plate prevent backward, disengaging movement of the spring structure. With the protuberances of the spring structure so engaged with detents at both ends of the plate, the spring structure is held firmly in place in channel 26. Protuberances 40 and detents 42 prevent longitudinal movement of the spring structure. Bottom wall 28 of the channel prevents downward movement of the spring structure. Top wall 34 of the channel prevents upward movement of the spring structure.

Considering that the protuberances at each end of the spring structure prevent longitudinal movement of the spring structure in only one direction, a single set/pair of two-way protuberances 402 can be located away from the ends of the spring structure, for example toward the middle of the length of the spring structure, as indicated in dashed outline in FIG. 7B. Detents 42 are positioned correspondingly along the lengths of side walls 30 of the channel. Where protuberances 402 are positioned away from the ends of the spring structure, the detents can be structured to provide interfering, arresting surfaces for coacting with corresponding surfaces of the protuberances such that each combination of detent and protuberance is effective to prevent movement in either of the longitudinal directions, e.g. two-way movement, along the length of channel 26. Where the protuberance/detent surfaces are suitably designed, and where springs 38 exert sufficient resilient force, a single two-way protuberance 402, acting with a single two-way detent, away from the ends of the channel, can be effective to arrest movement of the spring structure in two, namely both, longitudinal directions. Indeed, so long as the detent and protuberance are suitably configured to arrest movement in both longitudinal directions, the protuberance can be located anywhere along the length of the spring structure 14, including at the ends of the spring structure, and the detent can be correspondingly located anywhere along the length of the channel, even at or proximate the end of the channel, so long as the detent is suitably restrictive, with respect to the corresponding protuberance, to retain the spring structure in the channel.

In view of protuberances 40 and cooperating detents 42, along with channel 26, including side walls 30 and overhanging top walls 34, spring structure 14, including bands 36A, 36B, is effectively confined in channel 26. The spring structure is effectively prevented from moving longitudinally by the combination of protuberances 40 and detents 42. The spring structure is effectively prevented from moving laterally by side walls 30 of the channel. The spring structure is effectively prevented from moving vertically by bottom wall 28 and overhanging top walls 34. Thus, once the spring structure is inserted into the channel, and protuberances 40 are engaged with detents 42, the spring structure is effectively locked into position in channel 26. In such position, bands 36A, 36B extend across portions of the respective apertures 22 as illustrated in e.g. FIGS. 1–3.

As shown in the various drawings, springs 38 extend between the respective bands 36A, 36B, and thus bias the bands with respect to each other. Thus, e.g. when squeezing force is applied to the spring structure to reduce the overall width of the spring structure thereby to enable the spring structure to be inserted into channel 26, springs 38 are effectively biasing the bands against each other, such that a force exerted against a first one of the bands, and directed toward the other of the bands, is transferred at least in part to the other band, whereby the physical properties of the bands interact with each other when such force is applied.

Thus, with the spring structure fully inserted into channel 26, springs 38 position bands 36 solidly against the side walls of the channel at locations where the bands are not passing through apertures 22. With the bands solidly against the side walls of the channel, the outwardly-disposed walls 46 of the bands are in surface-to-surface contact with side walls 30 of the channel. The outwardly-disposed walls 46 of the bands, the spring-loading of the bands, the respective rows of apertures 22, overhanging top walls 34, protuberances 40, detents 42, and springs 38 are thus all correspondingly sized, arranged and configured with respect to each other such that bands 36 are trapped between the side walls, the channel bottom or elements of a channel bottom, the overhanging top walls, and the springs such that the bands, without external forces applied, extend along a path wherein outwardly-disposed walls 46 of the bands extend alongside, and in surface-to-surface engagement with, side walls 30 of the channel. Since imaginary extensions of the side walls of the channel are displaced inwardly, into the apertures, of the aperture side walls by about 1 mm, the outwardly-disposed side walls of the bands also are displaced inwardly of the aperture side walls by a distance "D" of about 1 mm, and thus extend across corresponding portions of the projected cross-sections of the respective apertures.

Figure 6:
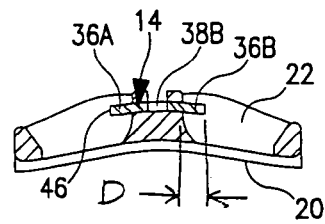
FIG. 6 shows a cross-section of the bone treatment plate assembly of FIGS. 1–4 and is taken at 6—6 of FIG. 4.

FIG. 6 shows a cross-section of the spinal plate assembly of FIGS. 1–4 at an aperture 22. Thus, FIG. 6 shows bands 36A, 36B extending into apertures 22, as well as showing a spring 38B biasing the bands into such position.

Figure 8:
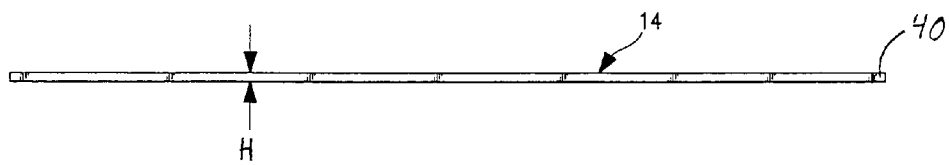
FIG. 8 shows a side elevation of the spring structure of FIG. 7A.

FIG. 8 shows a side view of the spring structure, illustrating the preferred uniform height "H" of the spring structure along the length of the spring structure.

Figure 11:
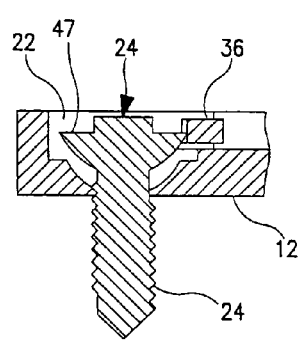
FIG. 11A is a cross-section of a bone treatment plate assembly as in FIGS. 1–4, showing the band deflected by the passing of the head of a bone screw in contact with the band.
FIG. 11B is a cross-section as in FIG. 11A wherein the head of the bone screw has passed the bottom of the band thus to enable the band to revert toward or to its undeflected and blocking position over the head of the bone screw.
Figure 11:
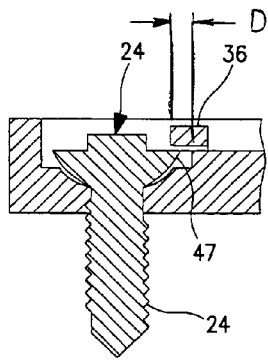

FIGS. 11A and 11B illustrate the process by which a band 36 is flexed or deflected, or otherwise caused to move in treatment plate assembly 10, when a bone screw 24 passes the band. FIGS. 11A and 11B further illustrate the interference in a withdrawal path of the screw, provided by the band after the head of the screw has been driven past the band and the band has returned to the undeflected or less deflected condition.

Referring to FIG. 11A, as a bone screw is advanced through an aperture 22, the spring biasing of the band is effective, automatically and as a consequence of driving the bone screw through the respective aperture and into bone structure of a recipient user, to respond to side force applied by an interfering element 47 such as the outer portion of the head of the bone screw by resiliently moving transversely of the length of the band, and in a direction away from the interfering element, and by the band resiliently returning to a position over the interfering element after the interfering element passes the band. After returning over the interfering element, the position of the band over the interfering element is effective to inhibit withdrawal of the bone screw past the band and out of the bone treatment plate assembly.

Looking specifically at FIG. 11A, as the bottom surface (e.g. interfering element) of the outer portions of the head of the bone screw engages the top outer corner of the band, the beveled or conical bottom surface of the screw head urges the band out of interfering alignment under the screw head. Once the screw head, as an interfering element of the screw, has moved past the band, the band automatically returns to an interfering, blocking position over the outer edge of the screw head as shown in FIG. 11B. Such interfering, blocking position over the screw head is effective to interfere with, typically to block, withdrawal of that screw past that band. Thus, the band serves as a safety device preventing withdrawal of the bone screw from the bone, and from the bone treatment plate assembly.

FIGS. 12 and 13 illustrate a further family of embodiments of bone treatment plate assemblies of the invention. In the embodiments of FIGS. 12 and 13, plate 12 is substantially as shown and described in the previous embodiments. As noted hereinabove, spring structure 14 is shown as a plurality of shortened band-spring combinations 48, with spacers 50 disposed between the respective band-spring combinations, the end combinations 48 embodying protuberances 40, which are received in two-way detents in channel 26. Thus, spring structure 14 in FIGS. 12 and 13 is expressed as intermittent placement of the band-spring combinations along the length of the plate, whereby channel 26 is effectively intermittent, with spacers 50 acting as barriers between the intermittent expressions of the channel.

In a family of embodiments (not shown), channel 26 can be intermittent, namely expressed intermittently, and exist adjacent only e.g. some or all of apertures 22. In such embodiments, bands 36A, 36B are held in channel elements which extend e.g. downwardly from top surface 18 of plate 12, and which channel elements thus define the band paths. Springs 38 are employed as desired, such as in FIG. 12. Protuberances 40 are not needed because end walls of the intermittent expressions of the channels prevent longitudinal movement of the bands, whereby the retaining functions of the protuberances and detents are typically provided by material of the plate. However, in such instances, suitable expressions of top walls 34 are included in each expression of the channel both to accommodate entry of the spring structure through the top of the channel, and to prevent inadvertent release of the spring structure through the top of the channel.

FIGS. 12 and 13 illustrate a plurality of band-spring combination structures positioned in the channel, which can also be considered as intermittent expressions of a channel between spacers 50, and disposed alongside the respective pairs of apertures, with spacers 50 positioned between respective adjacent band-spring combinations so as to inhibit substantial longitudinal movement of the band-spring combinations, and to provide end surfaces, at the ends of the spacers, against which the springs can flex inwardly as a bone screw is driven past the respective band. As shown, each band-spring combination includes a pair of bands 36 on opposing sides of the combination element, and first and second 2-direction folded leaf springs 38 at opposing ends of the combination element. In assembly 10, each band-spring combination is sufficiently long to extend along substantially the full length of an adjacent aperture 22 and to engage the side walls 30 at each end of the respective aperture.

FIGS. 12 and 13 show a separate band-spring combination 48 for deployment adjacent each pair of apertures 22. As desired, fewer such band-spring combinations can be used wherein at least one such band-spring combination can extend across two or more such pairs of apertures.

Since bone treatment plate assemblies of the invention are to be used within living bodies, all materials used in the bone treatment plate assemblies must be compatible with, and safe for use inside, the living body. In that regard, preferred material for bone treatment plate 12, spring structure 14, 48 and springs 38, is titanium, or titanium alloy, for example titanium-aluminum alloy. A specific titanium aluminum alloy referred to in ASTM F-136 is (Ti 6AL-4V). Other titanium alloys, compatible for use in the living body, are contemplated. Preferred materials for bands 36 have a desired level of resilient flexural capacity. Safety is typically controlled by composition and structure. In this analysis, exemplary structure is shown in the drawings herein; and composition is the variable being analyzed for safety.

Plate 12 has a length sufficiently long to span at least two vertebrae, and width and thickness sufficiently great to provide resistance to bending and torsion forces. Accordingly, where plate 12 is composed of one of the above referred-to materials, typical dimensions are as follows. Typical length is at least 20 mm, up to as great as about 120 mm or more. Width is typically about 15 mm to about 20 mm. Nominal thickness is typically about 2 mm to about 3.5 mm. The bottom of channel 26 is typically about 0.7 mm to about 1.5 mm from the top surface of the plate. Typical nominal depth of channel 26, from the bottom of the channel to any overhanging top wall, is about 0.5 mm. Such dimensions are, of course, exemplary only and not not limiting and, given the above exemplary dimensions, those skilled in the art can vary such dimensions according to specific structure of respective plates and plate assemblies.

In addition, the plate assembly materials must perform the required physical functions of flexing enough, when properly positioned over apertures 22, to let the bone screws pass below the bands without exceeding the flexural limits, collectively, of the band materials or the springs, and must return to blocking positions over the screws or other control structure after passage of the bone screws. Such flexural properties are based on physical properties inherent in the material compositions, in combination with the physical cross-sections of the bands and springs.

The resilient properties can be provided by bands 36, by springs 38, or by a combination of bands 36 and springs 38. Thus, bands 36 can be substantially non-flexible and substantially all the resilience can be provided by the flexibility of springs 38. In the alternative the structures shown as springs 38 can be substantially non-flexible, namely can perform a rigid blocking function once installed in channel 26, whereby most, or substantially all, of the resilience is provided by bands 36. Typically, the ability of bands 36 to move, in response to advance of a bone screw, is provided in part by each the band and at least one spring, preferably all of the springs, working cooperatively together.

In preferred embodiments, but not all embodiments, bands 36 and springs 38 are fabricated from a single piece of material whereby the inherent physical properties of the bands and the springs are the same. Typically, the resilience in such combination is provided by the combination of springs 38 and bands 36. The resiliences provided by the respective bands and springs in such combination are nevertheless dependent on the respective widths and thicknesses of the bands and springs, as well as on the angles expressed between the springs and the bands at any given time. Thus, considering the element widths suggested in FIG. 10A, assuming common material, one would expect substantially all the resilient bending to take place in springs 38, at least relative to bands 36.

The greater the included acute angle $\alpha$ between a band and a respective spring 38, the relatively greater the spring constant/degree of resistance which the spring can exert against a force squeezing the bands 36A, 36B toward each other. The smaller the included angle $\alpha$, the relatively less the spring constant/degree of resistance. Thus, by varying angle $\alpha$ and/or spring width "W" and/or band width "W3", the springs and bands can be engineered for a wide range of desired degrees of resilient restoration force to be provided by the respective bands and springs.

In some embodiments, such as where plate 12 has only a single row of apertures 22, width "W3" of band 36B can be greater than width "W3" of band 36A. In such instance, typically band 36B extends across apertures 22 and band 36A serves as a connector to connect springs 38 together.

Since the spring structure in such embodiments is thus asymmetric with respect to widths "W3" of bands 36, it is desirable to fabricate spring structure 14 so as to assure proper orientation of the spring structure in channel 26. To that end, detents 42 can be fabricated only in the side wall 30 which extends along the apertures 22; and protuberances 40 can be fabricated only on the wider one of the bands 36 which is to be juxtaposed against and over apertures 22, whereby the other band is devoid of protuberances.

In the alternative, other structural and/or dimensional relationships can be employed to assure proper orientation of spring structure 14 in channel 26.

Certain materials which are not generally considered as having resilient, spring-like properties can, when fabricated into sufficiently small cross-sections, perform the desired resiliently flexural spring function of the springs or the bands. For example and without limitation, bands 36 can employ titanium compositions, titanium alloy compositions such as titanium-aluminum alloy compositions such as the above-mentioned specific alloy, or other titanium alloys, or stainless steel compositions which, in sufficiently small cross-section, can exhibit the desired resilient spring-like properties. Other materials can be used as bands 36 and springs 38 so long as such materials satisfy the above safety and performance requirements.

Any of the plastic materials known to be safe for use in living human or animal bodies, as applies, as implantable plastics, and which have suitable hardness, rigidity, and resilience, can be employed for fabricating bands 36 and springs 38. As with the metals, such materials must be both bio-stable and bio-compatible.

As such plastics, there can be mentioned, for example and without limitation, polyetherimide copolymer such as ULTEM®,
acetal copolymer, polyethersulfone, also known as polyarylsulfone, such as RADEL A®, polyarylethersulfone such as RADEL R®, polycarbonate, ultra high molecular weight polyethylene, polyetheretherketone, also known as PEEK, available from Boedecker Plastics, Inc. Shiner, Tex., polyaryletherketone, also known as PEEK-OPTIMA®.

Such materials can be filled or unfilled, and can employ the usual additives, including processing aids, so long as the resultant composition is suitable as an implantable plastic for use in a living, e.g. human body.

As a result of the structures of apertures 22, channel side walls 30, and spring structure 14, along with proper positioning of protuberances 40 in detents 42, when a bone screw, which properly fits an aperture 22, is driven through the aperture 22, the head of the bone screw impacts the respective band 36 as shown in FIG. 11A, and forces the band in a width-wise transverse direction away from the center of the aperture in order that the head of the bone screw can pass the band. Since the band is readily and resiliently moved, against resistance of springs 38, and since the bone screw is already embedded in bone material of the recipient user by the time the screw head reaches the band, the band moves in response to the urging of the head of the bone screw, as shown in FIG. 11A. When the head of the bone screw passes below the bottom of the band, the band is no longer being held in the moved position, and therefore resiliently returns toward the position occupied prior to being moved, thereby setting up a potential interference between the band and the screw, of more or less about 1 mm, which interference is implemented if and when the screw begins to back out of, or withdraw from, the spinal plate.

The invention contemplates that bands 36 can be arranged in other than a resting and straight condition when not being forced sideways by heads of bone screws. Thus, the bands can be under a degree of constant stress, e.g. pre-stressed condition, wherein the level of stress changes as the head of the screw passes, and then reverts to the previous level of stress, or some other related stress, after the screw head passes. In general, springs 38, even without stress from a bone screw, typically exert a relatively modest degree of force urging bands 36 against the side walls 30 of channel 26.

Bands 36 can be arranged in a non-straight, e.g. curvilinear or angled e.g. folded, configuration when not being moved by a screw head or other interfering element, and can still move with respect to the bone screw as the bone screw is driven past the band.

Likewise, channel 26 can be intermittent, and can exist only adjacent apertures 22. FIGS. 12 and 13 illustrate an effectively intermittent use of spring structure 14, effectively defining spaced channel pockets, wherein spacers 50 obviate spring structure 14 extending the full length of plate 12, and wherein each band-spring combination 48 structure 14 operates within a fabricated individual channel pocket in the plate. Each band-spring combination also embodies its own spring restoration properties. As suggested by FIG. 13, where a band-spring combination is confined within such a pocket, having both side walls and end walls, no protuberance 40 or detent 42 need be employed at the band-spring combination. Namely, side walls 30, and end walls, of the pocket suitably retain the band-spring combination from longitudinal and transverse movement with respect to the plate and pocket, and suitable top wall 34 and/or bottom wall 28 structure in the channel prevent upward and downward movement of the spring structure with respect to the channel.

In the alternative, protuberances 40 and detents 42 can be used with such intermittent structure as desired. For example, where protuberances 40 are employed on each band-spring combination, albeit of relatively shorter length, in combination with respectively located detents to cooperate with the protuberances on each band-spring combination, the relatively shorter band-spring combinations can be employed without use of intervening spacers 50.

If desired, some interfering element other than the head of the screw can be used to activate and release the band. For example, an interfering element (not shown) can be designed into the screw below the screw head, above the screw head, or otherwise, for the purpose of activating movement and release of the band.

Whatever the positions of the bands, whatever the interfering element on the screw, which interfaces with the band, once the band is released from the movement caused by the respective interfering element, and the band thus returns to the position which it occupied prior to having been moved, the band is positioned above, over, and in an interfering and blocking position with respect to, a path which some portion of the screw must traverse in order to withdraw from the spinal plate assembly. Referring to FIG. 11B wherein the head of the screw has passed below the bottom of the band, and wherein the band has thus returned toward or to the pre-stressed position, the band is seen to overlie a portion of the surface of the head of the screw, such that if the screw begins to withdraw e.g. away from the plate, the head of the screw impacts the bottom of the band. As withdrawal of the screw progresses such that the screw reaches the bottom of the band, the band, being supported by overhanging top walls 34, or other top wall-type structure, prevents the screw from further withdrawing from the plate.

As seen in FIG. 11A, when the screw is driven through the plate, e.g. and into bone material of a recipient user of the bone treatment plate assembly, the force applied by the upwardly-extending angular bottom surface of the screw automatically pushes the band aside as the head of the screw pushes against and passes the band. Once the head of the screw passes the band, the band is automatically restored toward or to the unmoved position over the head of the screw, illustrated in FIG. 11B. Thus, in bone treatment plate assemblies of the invention, driving the bone screw, and thereby mounting the bone treatment plate assembly in the body of a recipient user thereof, automatically moves, optionally flexes, the band, as a blocking member, out of the way of insertion of the bone screw, and then the blocking member/band automatically moves to a blocking, locking position over the head or other control structure of the screw, thereby automatically activating the blocking and locking feature of the bone treatment plate assembly to block withdrawal of the bone screw, and thus to lock the bone screw in the assembly and retain joinder of the bone screw to the respective bone of the recipient user/patient. Such bone screw can, of course, be released for removal by manually or otherwise intentionally moving or flexing the band away from the screw, and removing the screw while the band is thus held in the moved or flexed condition.

Figure 2:
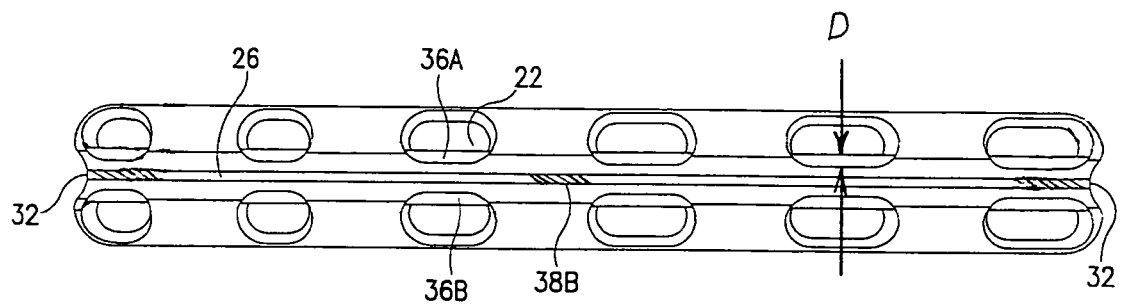
FIG. 2 shows a top view of the bone treatment plate assembly illustrated in FIG. 1.
Figure 3:
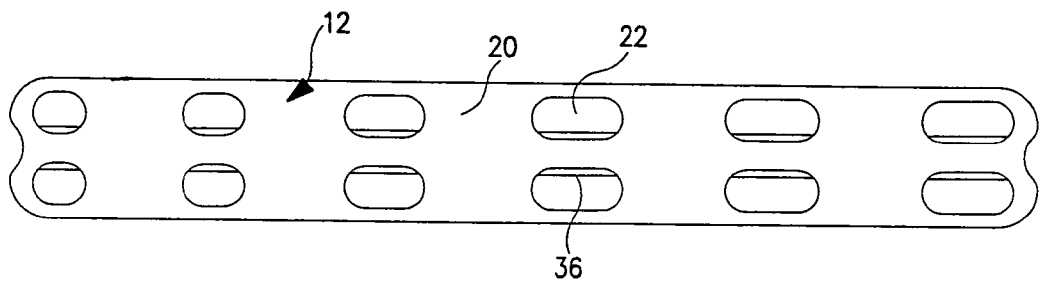
FIG. 3 shows a bottom view of the bone treatment plate assembly illustrated in FIG. 1.

In preferred embodiments of the invention, all of apertures 22 are slot-shaped in that, e.g. in projection, each aperture has an elongate dimension and a shorter cross-dimension. In some embodiments, two of the apertures are relatively lesser lengths, optionally circular, and serve as support apertures, and the remaining apertures are relatively greater lengths, as slots or slot-shaped, and serve as settle apertures, providing for the bone structure to settle while being advantageously held by the bone treatment plate. In still other embodiments, all of apertures 22 are circular. As seen in FIGS. 1 and 2, typically each aperture along the length of the bone treatment plate assembly can be progressively longer/shorter than the adjacent apertures in the same row, to accommodate the progressively increasing distance moved by respectively more upwardly-disposed ones of the vertebrae being treated by the plate assembly. All of the slots have commonly oriented axes along the elongate dimensions of the slots. Preferably, all apertures 22 are slot apertures having relatively longer lengths and relatively shorter widths.

Typical length increments for adjacent apertures are about 1 mm. Accordingly, in a plate 12 as in FIGS. 1–4 having 6 apertures per row, the length differential between the longest and shortest apertures 22 can be, for example, about 5 mm. The exact and actual length differentials can be somewhat different, depending on the specific use contemplated for the respective plate 12.

In an embodiment not shown, all of the bone screw apertures 22 are circular. Accordingly, such assembly provides for fixed positioning of the bone being supported. Otherwise, all features of the spinal plate assembly are substantially the same as the elements and features of the assemblies of e.g. FIGS. 1–13. Thus, bands 36 and springs 38 all employ the same principles illustrated hereinabove.

Typically, spinal plate assemblies of the invention have two rows of apertures 22. And while the spinal plate assemblies illustrated in the drawings show 2 rows of bone screw apertures, the invention can well be utilized with any desired number of rows of apertures, and any desired number of apertures per row, or any other arrangements of aperture array which enable desired post-procedural movement of the vertebrae without adding substantial bone-to-plate stress as a result of such relative movement.

Those skilled in the art will now see that certain modifications can be made to the apparatus and methods herein disclosed with respect to the illustrated embodiments, without departing from the spirit of the instant invention. And while the invention has been described above with respect to the preferred embodiments, it will be understood that the invention is adapted to numerous rearrangements, modifications, and alterations, and all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. A bone treatment plate assembly, comprising:
   (a) a bone treatment plate (12), said bone treatment plate having a length, and comprising a top and a bottom, and a plurality of bone-fastener-receiving apertures, said bone treatment plate further comprising a thickness between the top and the bottom, a channel extending alongside respective ones of the apertures, said channel having a collective length, and a side wall (30), said side wall of the channel having an opening therein extending into a respective said one of the fastener-receiving apertures; and
   (b) spring structure (14) in said channel, said spring structure having first and second ends, a length, a structure top and a structure bottom, and a structure height (H) therebetween, said spring structure further comprising
      (i) first and second bands (36A, 36B) each having first and second ends, a band top, and a band bottom associated with the structure top and the structure bottom, said bands having respective lengths thereof, said first and second bands each having an outer surface (46) facing outwardly of said spring structure (14), and an inner surface, the inner surfaces facing each other and facing inwardly into said spring structure, said first and second bands defining a width (W1) of said spring structure between the outer surfaces (46), and extending along the length of said channel in said bone treatment plate, and
      (ii) springs (38) spaced along the length of said spring structure, said springs extending between and being connected to said bands, and having spring lengths extending between the first and second bands, said springs having spring tops and spring bottoms, opposing spring sides, spring heights between the spring tops and the spring bottoms, spring widths (W) between the opposing spring sides, angles α being defined between the springs (38) and the inner surfaces of said bands (36), and angles β being defined between the band tops and the spring tops, said springs urging said spring structure into engagement with the side wall of the channel, ratio of the widths (W) of the springs to the heights of the springs being less than 1/1, whereby, when a squeezing force is imposed on said spring structure (14), squeezing said first and second bands (36) toward each other, sufficient to assemble said spring structure (14) to said bone treatment plate (12), said springs (38) resiliently deflect so as to accommodate reduced width (W1) of said spring structure (14) in preference to deflecting in a direction corresponding to height (H), such that the response of said spring structure (14) to such squeezing force is a preferential resilient change in magnitude of angle α relative to change in magnitude of angle β.

2. A bone treatment plate as in claim 1 wherein, when such squeezing force is imposed on said spring structure, change in magnitude of angle β is substantially zero.

3. A bone treatment plate assembly as in claim 2 wherein said spring structure comprises plastic composition which is safe for use in living human or animal bodies, as an implantable plastic, and wherein said spring structure has suitable strength, rigidity, and deflection properties to block screw withdrawal in a routine implant use environment.

4. A bone treatment plate assembly as in claim 1 wherein the ratio of spring width to spring height is no more than 0.8/1.

5. A bone treatment plate assembly as in claim 1 wherein the ratio of spring width to spring height is about 0.15/1 to about 0.7/1.

6. A bone treatment plate assembly as in claim 5 wherein said spring structure comprises plastic composition which is safe for use in living human or animal bodies, as an implantable plastic, and wherein said spring structure has suitable strength, rigidity, and deflection properties to block screw withdrawal in a routine implant use environment.

7. A bone treatment plate assembly as in claim 6 wherein the plastic composition of said spring structure comprises one or more materials selected from the group consisting of polyetherimide copolymer, acetal copolymer, polyethersulfone, polyarylethersulfone, polycarbonate, ultra high molecular weight polyethylene, polyetheretherketone, and polyaryletherketone, and blends and mixtures of said materials.

8. A bone treatment plate assembly as in claim 5 wherein said channel is expressed intermittently along the length of said plate.

9. A bone treatment plate assembly as in claim 8 wherein the compositions of said first and second bands comprise at least one of titanium, titanium alloy, and stainless steel.

10. A bone treatment plate assembly as in claim 5 wherein the composition of said spring structure comprises at least one of titanium, titanium alloy, and stainless steel.

11. A bone treatment plate assembly as in claim 5 wherein the compositions of said first and second bands comprise at least one of titanium, titanium alloy, and stainless steel.

12. A bone treatment plate assembly as in claim 1 wherein the ratio of spring width to spring height is about 0.2/1 to about 0.5/1.

13. A bone treatment plate assembly as in claim 1 wherein the ratio of spring width to spring height is about 0.25/1 to about 0.35/1.

14. A bone treatment plate assembly as in claim 1 wherein said springs are arranged in groups of at least two springs along said bands.

15. A bone treatment plate assembly as in claim 14 wherein said channel is expressed intermittently along the length of said plate.

16. A bone treatment plate assembly as in claim 14 wherein the composition of said spring structure comprises at least one of titanium, titanium alloy, and stainless steel.

17. A bone treatment plate assembly as in claim 14 wherein the compositions of said first and second bands comprise at least one of titanium, titanium alloy, and stainless steel.

18. A bone treatment plate assembly as in claim 1 wherein said springs are arranged in groups of at least three springs along said bands.

19. A bone treatment plate assembly as in claim 1 wherein said springs are arranged individually along the length of said spring structure.

20. A bone treatment plate assembly as in claim 1 wherein said springs comprise folded springs.

21. A bone treatment plate assembly as in claim 1 wherein said first and second bands, in combination with said springs, define a unitary structure derived from a single unitary work piece.

22. A bone treatment plate assembly as in claim 21 wherein the composition of said spring structure comprises at least one of titanium, titanium alloy, and stainless steel.

23. A bone treatment plate assembly as in claim 1 wherein said first and second bands extend along substantially the entirety of the length of the channel, said first and second bands collectively extending into and across portions of each of the bone-fastener-receiving apertures.

24. A bone treatment plate assembly as in claim 1, said side wall of said channel comprising a first side wall, said channel further comprising a second side wall, said bone treatment plate further comprising first and second rows of said bone-fastener-receiving apertures extending along the length of said bone treatment plate, said channel extending along the length of said bone treatment plate, said channel further comprising a second side, first and second overhanging top walls of said channel extending inwardly from said side walls of said channel, said overhanging top walls being effective to restrain movement of said spring structure out of said channel through the top of said channel.

25. A bone treatment plate assembly as in claim 24, said first and second elongate bands being urged by said spring structure against the respective first and second side walls of the channel, and thus across a portion of each respective aperture in the first and second rows.

26. A bone treatment plate assembly as in claim 24 wherein said spring structure comprises plastic composition which is safe for use in living human or animal bodies, as an implantable plastic, and wherein said spring structure has suitable strength, rigidity, and deflection properties to block screw withdrawal in a routine implant use environment.

27. A bone treatment plate assembly as in claim 1 wherein, as a such bone fastener is driven into any one of the bone-faster-receiving apertures, such bone fastener urges the respective said band to move, from a first position transversely of the length of said band, with corresponding flexing of said spring structure, from a first flexural condition, until such bone fastener moves past said band, whereupon said spring structure returns said band to a position wherein said band overlies and blocks the bone fastener and thereby inhibits withdrawal of the bone fastener past said band.

28. A bone treatment plate assembly as in claim 1 wherein said bands are sufficiently small in cross-section, and are properly positioned over said apertures, and wherein said spring structure is sufficiently resilient to let a bone fastener pass below a respective said band, with transverse movement of said band, and without exceeding any flexural limit of said spring structure, such that said spring structure then resiliently returns said band to a blocking position over such bone fastener.

29. A bone treatment plate assembly as in claim 1 wherein said springs comprise substantially straight line compression springs.

30. A bone treatment plate assembly as in claim 1, said springs comprising (i) at least three groups of springs wherein each group comprises at least two springs, and wherein spacing between the springs in a group is less than spacing between the groups, or (ii) at least 6 individual springs substantially equally spaced from each other.

31. A bone treatment plate assembly as in claim 1 wherein said first band (36A) has a first width (W3) and wherein said second band (36B) has a second width (W3) greater than the first width.

32. A bone treatment plate assembly as in claim 31, said bone treatment plate (12) comprising a single line of said bone-fastener-receiving apertures (22) extending along the length of said plate, said second band (36B) comprising at least one protuberance (40) extending outwardly from the respective said outer surface (46) of said band, said first band (36A) being devoid of protuberances on the respective outer surface (46), said channel side wall (30) comprising first and second side walls, said first side wall having openings extending into said bone-fastener-receiving apertures, said second side wall not having openings extending into said bone-fastener-receiving apertures, said first side wall (30) comprising at least one detent (42) receiving said at least one protuberance, said second side wall being devoid of detents adapted to receive said at least one protuberance.

33. A bone treatment plate assembly as in claim 1 wherein said spring structure comprises plastic composition which is safe for use in living human or animal bodies, as an implantable plastic, and wherein said spring structure has suitable strength, rigidity, and deflection properties to block screw withdrawal in a routine implant use environment.

34. A bone treatment plate assembly as in claim 33 wherein the plastic composition of said spring structure comprises one or more materials selected from the group consisting of polyetherimide copolymer, acetal copolymer, polyethersulfone, polyarylethersulfone, polycarbonate, ultra high molecular weight polyethylene, polyetheretherketone, and polyaryletherketone, and blends and mixtures of said materials.

35. A bone treatment plate assembly as in claim 1 wherein said channel is expressed intermittently along the length of said plate.

36. A bone treatment plate assembly as in claim 1 wherein the composition of said spring structure comprises at least one of titanium, titanium alloy, and stainless steel.

37. A bone treatment plate assembly as in claim 1 wherein the compositions of said first and second bands comprise at least one of titanium, titanium alloy, and stainless steel.

38. A bone treatment plate assembly as in claim 1, said bone-fastener-receiving apertures being spaced along the length of said bone treatment plate, said channel being elongate and extending along the length of said bone treatment plate, said spring structure comprising a plurality of band-spring combinations, each comprising ones of said bands (36) and ones of said springs (38), positioned in said channel, said band-spring combinations being disposed lengthwise of each other, and disposed alongside respective ones of said apertures, spacers being positioned between respective adjacent ones of said band-spring combinations so as to inhibit substantial longitudinal movement of said band-spring combinations.

39. A bone treatment plate assembly as in claim 38, said spacers being held in position in said channel by protuberances on ones of said bands and/or said spacers, which protuberances cooperate with detents in said channel.

40. A bone treatment plate assembly as in claim 1, said channel comprising a plurality of walls, including said side wall, extending at least intermittently along the length of said channel, at least one of said bands comprising a protuberance, said walls of said channel collectively comprising at least one cooperating detent, configured and positioned to receive the protuberance on the respective said band, said protuberance and said detent thereby being effective to arrest longitudinal movement of said spring structure along the length of the channel as said spring structure is moved along said bone treatment plate.

41. A bone treatment plate assembly as in claim 40, said at least one protuberance and said at least one cooperating detent being collectively configured to arrest longitudinal movement of the respective said spring structure or band-spring combination in either of two opposing longitudinal directions.

42. A bone treatment plate assembly as in claim 40, said at least one protuberance comprising a single protuberance and/or said at least one detent comprising a single detent.

43. A bone treatment plate assembly as in claim 1, said channel comprising a plurality of walls, including said side wall, extending along the length of said channel, at least a first protuberance extending from said first band, at least a second protuberance extending from said second band, said walls of said channel collectively comprising at least first and second detents, configured and positioned to receive the protuberances on the first and second bands, the combination of the first and second protuberances and the first and second detents being effective to arrest longitudinal movement of said spring structure along the length of the channel as said spring structure is being assembled with said bone treatment plate.

44. A bone treatment plate assembly as in claim 43 wherein said detent arrests longitudinal movement of said spring structure when the entirety of the length of said spring structure has been received into said channel.

45. A bone treatment plate assembly as in claim 1, said channel comprising a plurality of walls, including said side wall, extending along the length of said channel, first and second protuberances extending from said bands on opposing sides of said spring structure and toward respective ones of said walls of said channel, said walls of said channel comprising at least first and second detents, configured and positioned to receive the protuberances, the combination of the first and second protuberances and the first and second detents being effective to arrest longitudinal movement of said spring structure along the length of the channel.

46. A bone treatment plate assembly as in claim 45, said first and second protuberances extending outwardly from the outer surfaces of said bands.

47. A bone treatment plate assembly as in claim 46, said first and second protuberances being disposed at the first end of said spring structure.

48. A bone treatment plate assembly as in claim 46, further comprising third and fourth protuberances at the second end of said spring structure, and cooperating third and fourth detents in said walls of said channel.

49. A bone treatment plate assembly, comprising:
  (a) a bone treatment plate (12), said bone treatment plate comprising a top and a bottom, and a plurality of bone-fastener-receiving apertures, said bone treatment plate further comprising a thickness between the top and the bottom, a channel extending alongside respective ones of the apertures, said channel having a collective length, and having walls extending at least intermittently along the length of the channel; and
  (b) spring structure (14) in said channel, said spring structure (14) having first and second ends, a length, a structure top and a structure bottom, and a structure height (H) therebetween, said spring structure further comprising
    (i) first and second bands (36) each having first and second ends, a band top, and a band bottom associated with the structure top and the structure bottom, said bands having respective lengths thereof, said first and second bands each having an outer surface (46) facing outwardly of said spring structure, and an inner surface, the inner surfaces facing each other and facing inwardly into said spring structure, said first and second bands defining a width (W1) of said spring structure between the outer surfaces (46), and extending along the length of said channel in said bone treatment plate, and
    (ii) springs (38) spaced along the length of said spring structure, said springs extending between, and being connected to said bands, and having spring lengths extending between the first and second bands, said springs having spring tops and spring bottoms, opposing spring sides, spring heights between the spring tops and the spring bottoms, spring widths (W) between the opposing spring sides,
  at least one of said bands comprising a protuberance, said walls of said channel collectively comprising at least one detent configured and positioned to receive the protuberance on the respective said band, the combination of said at least one protuberance and said at least one detent being effective to arrest longitudinal movement of said spring structure along the length of the channel as said spring structure is advanced along said channel.

50. A bone treatment plate assembly as in claim 49, said bands comprising first and second protuberances extending from said bands at or proximate the first ends of the bands, and third and fourth protuberances extending from said bands at or proximate the second ends of the bands, said first, second, third, and fourth protuberances collectively being effective, in combination with said walls of said plate (12), and wherein said spring structure is otherwise confined with respect to the channel, to arrest longitudinal movement of said spring structure with respect to the channel.

51. A bone treatment plate assembly as in claim 49, angles α being defined between the springs (38) and the inner surfaces of said bands (36), and angles β being defined between the band tops and the spring tops, ratio of the widths (W) of the springs to the heights of the springs being less than 1/1, whereby response of said spring structure (14) to a squeezing force, squeezing said bands (36) toward each other, is a preferential change in magnitude of angle α relative to change in magnitude of angle β.

52. A bone treatment plate assembly as in claim 51 wherein the ratio of spring width to spring height is about 0.15/1 to about 0.7/1.

53. A bone treatment plate assembly as in claim 49 wherein the ratio of spring width to spring height is about 0.2/1 to about 0.5/1.

54. A bone treatment plate assembly as in claim 49 wherein said springs are arranged in groups of at least two springs along said bands.

55. A bone treatment plate assembly as in claim 49 wherein the compositions of said bands are selected from the group consisting of titanium, titanium alloy, and stainless steel.

56. A bone treatment plate assembly as in claim 49 wherein said springs comprise substantially straight line compression springs.

57. A bone treatment plate assembly as in claim 49, said springs comprising (i) at least three groups of springs wherein each group comprises at least two springs, and wherein spacing between the springs in a group is less than spacing between the groups, or (ii) at least 6 individual springs substantially equally spaced from each other.

58. A bone treatment plate assembly as in claim 49 wherein said first band (36A) has a first width (W3) and wherein said second band (36B) has a second width (W3) greater than the first width.

59. A bone treatment plate assembly as in claim 49 wherein said spring structure comprises plastic composition which is safe for use in living human or animal bodies, as an implantable plastic, and wherein said spring structure has suitable strength, rigidity, and deflection properties to block screw withdrawal in a routine implant use environment.

60. A bone treatment plate assembly as in claim 59 wherein the plastic composition of said spring structure comprises one or more materials selected from the group consisting of polyetherimide copolymer, acetal copolymer, polyethersulfone, polyarylethersulfone, polycarbonate, ultra high molecular weight polyethylene, polyetheretherketone, and polyaryletherketone, and blends and mixtures of said materials.

61. A bone treatment plate assembly as in claim 49 wherein the composition of said spring structure comprises at least one of titanium, titanium alloy, and stainless steel.

* * * * *